United States Patent [19]

De Muylder

[11] 4,041,171

[45] Aug. 9, 1977

[54] OCTYL THIOBENZOATE USED AS AN ACARICIDE

[75] Inventor: Jean Marie De Muylder, Kraainem, Belgium

[73] Assignee: Societe d'Etudes et de Realisations Scientifiques en Abrege S.E.R.E.S.C.I.S.P.R.L., Brussels, Belgium

[21] Appl. No.: 645,070

[22] Filed: Dec. 29, 1975

[30] Foreign Application Priority Data

Jan. 2, 1975 United Kingdom ............... 00033/75

[51] Int. Cl.$^2$ ............................................. A01N 9/12
[52] U.S. Cl. .................................................. 424/301
[58] Field of Search ..................... 424/301; 260/455 R

[56] References Cited

U.S. PATENT DOCUMENTS 3,254,106   5/1966   Godfrey ........................... 260/455 R

OTHER PUBLICATIONS

*Chemical Abstracts* 72:20853v (1970).
*Chemical Abstracts* 60:P3442a (1964).

*Primary Examiner*—Leonard Schenkman
*Attorney, Agent, or Firm*—Sughrue, Rothwell, Mion, Zinn and Macpeak

[57] ABSTRACT

This invention relates to acaricidal and ovicidal compositions containing octyl thiobenzoate or phenyl thiobenzoate as active ingredient.

7 Claims, No Drawings

OCTYL THIOBENZOATE USED AS AN ACARICIDE

BRIEF DISCLOSURE OF THE INVENTION

This invention relates to acaricidal and ovicidal compositions for the treatment of human beings, animals and plants.

It has been found that compounds of the following general formula:

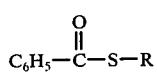

$$C_6H_5-\overset{\overset{O}{\|}}{C}-S-R \qquad (I)$$

in which R represents an octyl or phenyl radical, i.e. octyl thiobenzoate and phenyl thiobenzoate, which are known compounds, have remarkable acaricidal and ovicidal properties.

This invention relates therefore to topical compositions having an acaricidal and ovicidal activity, said compositions containing a compound of formula (I), together with a suitable vehicle or excipient.

The compounds of formula (I) are particularly active against mites of various morphology, physiology and ecology, such as the itch mite (*Sarcoptes scabiei*), blood sucking animal ticks (such as *Ixodes ricinus*) and soil or plant mites (such as *Platynothrus peltifer*).

TESTS

The following tests have shown the acaricidal and ovicidal properties of two compounds of formula (I), i.e. octyl thiobenzoate (DB 167) and phenyl thiobenzoate (DB 168) in comparison with known acaricides, i.e. benzyl thiobenzoate (DB 169) and phenyl chlorophenylthiocetate (DB 166).

A. Rearing of mites

*Platynothrus peltifer* was extracted from an oak litter by Berlèse-Tullgren funnels and reared under constant conditions of temperature and relative humidity (20° C, 60% relative humidity).

Engorged female ticks (*Ixodes ricinus*) were detached from a cow and placed in a room conditioned to 28° C and 90% relative humidity, where they were kept 30 cm under four "daylight" fluorescent strips. This artificial light provided a day-length of 15 hours. Under these conditions of storage, the hatching of the eggs occured from 27 to 31 days after laying. The larvae were used in the tests.

B. Test method used

The sprayer used for the assays pulverized 1.5 ml of each tested compound at a constant pressure of compressed air. The mites were placed on a filter paper in a 5 cm diameter dish receiving spray at a distance of 30 cm and with an angle of 30°. Treated mites were placed in 3.5 cm diameter capsules. The bottom of the capsules was covered with a mixture of animal charcoal and plaster of Paris which allows, by adding a little water, to maintain adequate humidity for several days.

The tested compounds were dissolved in dimethyl sulfoxide (D.M.S.O.) which showed good solvent properties combined with low toxicity per se.

Initial screening tests led to the following doses used in the tests: 1%, 2%, 4%, 5.5%, 7%, 9% and 10% for *Platynothrus peltifer* and 0.5%, 1%, 2%, 3%, 4% and 5% for *Ixodes ricinus*.

Four replicates of fifteen Platynothrus peltifer and three replicates of twelve *Ixodes ricinus* were used per dose and per tested compound. Untreated mites and DMSO-treated mites have been used as control.

Each day, dead animals were counted and eliminated. As a first test showed that mortality does not vary after the sixth day, the tests were limited to a ten day period.

C. RESULTS

Table I shows the mortality in *Platynothrus peltifer* on the tenth day by the different concentrations of tested products, whereas Table II gives the mortality in *Ixodes ricinus* under the same conditions.

TABLE I

| Tested compounds | Mite : Platynothrus peltifer Dose (%) | Mortality (%) |
| --- | --- | --- |
| DB. 167 | 1 | 0 |
|  | 2 | 2.3 |
|  | 4 | 27.6 |
|  | 5.5 | 40.9 |
|  | 7 | 53.3 |
|  | 9 | 84.4 |
|  | 10 | 88.9 |
| DB. 168 | 1 | 0 |
|  | 2 | 11.1 |
|  | 4 | 33.3 |
|  | 5.5 | 83.7 |
|  | 7 | 93.3 |
|  | 9 | 97.7 |
|  | 10 | 100.0 |
| DB. 169 | 1 | 0.7 |
|  | 2 | 0 |
|  | 4 | 7.1 |
|  | 5.5 | 9.3 |
|  | 7 | 7.0 |
|  | 9 | 60.0 |
|  | 10 | 50.0 |
| D.M.S.O. (solvent) |  | 0.3 |
| untreated |  | 0.1 |

TABLE II

| Compound | Tick mite : Ixodes ricinus Tested compound : DB 167 Dose (%) | Mortality (%) |
| --- | --- | --- |
| DB. 166 | 1 | 0 |
|  | 2 | 0 |
|  | 4 | 0.6 |
|  | 5.5 | 4.2 |
|  | 7 | 24.3 |
|  | 9 | 39.7 |
|  | 10 | 57.2 |
| DB. 167 | 0.5 | 0 |
|  | 1 | 23.3 |
|  | 2 | 46.7 |
|  | 3 | 60.0 |
|  | 4 | 90.1 |
|  | 5 | 100.0 |
| D.M.S.O. (solvent) |  | 0.3 |
| untreated |  | 0.1 |

TABLE III

| Compound | LD$_{50}$(%) Platynothrus peltifier | Ixodes ricinus |
| --- | --- | --- |
| DB. 166 | 7.8 | 9.5 |
| DB. 167 | 5.9 | 1.9 |
| DB. 168 | 3.8 |  |
| DB. 169 | 12.1 |  |

The following Table III shows the LD$_{50}$(%) of the tested compounds.

EXAMPLES

The following examples illustrate the preparation of the active compounds of formula I, as well as topical compositions containing the same.

EXAMPLE 1

Preparation of octyl thiobenzoate

A mixture of 120 ml (1 mol.) of benzoyl chloride and of 178 ml (1 mol.) of octylmercaptan is maintained at 140° C during 7 hours. The reaction mixture is then distilled under reduced pressure and the fraction boiling at 127° C under 0.4 Torr is collected.

217.8 g (0.87 mol.) of a liquid having the following properties are obtained:

Density: 0.986 at 20° C

Refractive index: 1.5312 at 20° C

Analysis: Sulfur: 12.76% (calculated: 12.81%).

EXAMPLE 2

Preparation of phenyl thiobenzoate

A mixture of 120 ml (1 mol.) of benzoyl chloride and 110 g (1 mol.) of thiophenol is maintained at 130° C during 7 hours. Nitrogen is then bubbled in the reaction mixture at 130° C during 3 hours. After cooling, 300 ml of toluene are added and the organic phase is first washed with water by decantation and dried on calcium sulfate. After evaporation of the solvent, the desired product is recrystallized from methanol. 72 g of phenyl thiobenzoate are obtained. M.P. 56° C.

Analysis: Sulfur: 15% (calculated: 14.96%).

Topical compositions according to this invention are described in the following examples 3 to 5.

EXAMPLE 3

| EMULSION | |
| --- | --- |
| Thiobenzoate of formula (I) | 2.5 g. |
| Benzyl alcohol | 2.5 g. |
| Triethanolamine laurylsulphate | 5 g. |
| Propylene glycol | 10 g. |
| Water ad. | 100 ml. |

EXAMPLE 4

| OINTMENT | |
| --- | --- |
| Thiobenzoate of formula (I) | 2.5 g. |
| Cutina (1) | 14 g. |
| Cetiol (2) | 15 g. |
| Benzyl alcohol | 2.5 g. |
| Preserving agent (3) | 1 g. |
| Water ad. | 100 g. |

(1) product consisting basically of an emulsible glyceryl monostearate manufactured and sold by HENKEL, Düsseldorf, Germany.
(2) product consisting basically of decyl oleate manufactured and sold by HENKEL, Düsseldorf, Germany.
(3) the preserving agent may be ethyl or butyl para-hydroxybenzoate.

EXAMPLE 5

| | Concentrated aqueous suspension |
| --- | --- |
| Octyl or phenyl thiobenzoate | 5 to 25 parts by weight |
| Non-foaming wetting agent | 10 to 30 parts by weight |
| Water q.s.ad. | 100 parts by weight |
| pH | 5 to 8 |

The non-foaming agent may be selected among the sorbitan fatty acid esters, the polyoxyethylene sorbitan fatty acid esters, the polyoxyethylene sorbitol esters, the polyoxyethylene alcohols and aryl ethers and the alkylarylsulfonates.

When used, the concentrated aqueous suspension must be diluted with water to a total weight of 1000 parts.

The diluted suspension may be used, for example, for spraying fruit trees in orchards, in order to kill the mites infesting the trees.

What is claimed is:
1. A process for treating animals or plants infested with acarid pests which comprises applying thereto an acaricidally effective amount of octyl thiobenzoate.
2. The process of claim 1 wherein said thiobenzoate is applied to human beings.
3. The process of claim 1 wherein said thiobenzoate is applied to animals.
4. The process of claim 1 wherein said thiobenzoate is applied to plants.
5. The process of claim 1 wherein said thiobenzoate is applied to fruit trees.
6. The process of claim 1 wherein said thiobenzoate is applied as an aqueous dispersion thereof containing a non-foaming wetting agent.
7. The process of claim 1 wherein said thiobenzoate is applied as an ointment containing said thiobenzoate and an ointment excipient.

* * * * *